(12) United States Patent
Suh et al.

(10) Patent No.: US 12,201,841 B2
(45) Date of Patent: Jan. 21, 2025

(54) IMPLANT SYSTEM AND METHOD

(71) Applicants: SAMSUNG ELECTRONICS CO., LTD., Suwon-si (KR); NORTHEASTERN UNIVERSITY, Boston, MA (US)

(72) Inventors: Junyeub Suh, Suwon-si (KR); Sangjoon Kim, Hwaseong-si (KR); Hui Fang, Hanover, NH (US); Jaehyeon Ryu, Brighton, MA (US)

(73) Assignees: Samsung Electronics Co., Ltd., Suwon-si (KR); NORTHEASTERN UNIVERSITY, Boston, MA (US)

( * ) Notice: Subject to any disclaimer, the term of this patent is extended or adjusted under 35 U.S.C. 154(b) by 299 days.

(21) Appl. No.: 17/551,696

(22) Filed: Dec. 15, 2021

(65) Prior Publication Data

US 2022/0193407 A1 Jun. 23, 2022

Related U.S. Application Data

(60) Provisional application No. 63/126,639, filed on Dec. 17, 2020.

(51) Int. Cl.
*A61N 1/05* (2006.01)
*A61N 1/36* (2006.01)

(52) U.S. Cl.
CPC ......... *A61N 1/3614* (2017.08); *A61N 1/0551* (2013.01); *A61N 1/36167* (2013.01); *A61N 1/36185* (2013.01)

(58) Field of Classification Search
CPC ................ A61N 1/3614; A61N 1/0551; A61N 1/36167; A61N 1/36185; A61N 1/0556;
(Continued)

(56) References Cited

U.S. PATENT DOCUMENTS

| 10,300,285 B2 | 5/2019 | Astrom et al. |
| 2003/0083724 A1* | 5/2003 | Jog ..................... A61N 1/0536 607/122 |

(Continued)

FOREIGN PATENT DOCUMENTS

| JP | 2014-23870 A | 2/2014 |
| JP | 2020-114348 A | 7/2020 |

(Continued)

*Primary Examiner* — Ankit D Tejani
*Assistant Examiner* — Joshua Brendon Solomon
(74) *Attorney, Agent, or Firm* — NSIP Law

(57) ABSTRACT

An implant system includes an electrode portion comprising plural electrodes to perform nerve stimulation and nerve sensing, an impedance controller configured to selectively connect the plural electrodes between a stimulator to perform nerve stimulation and a sensor to perform nerve sensing based on a control signal, and set an impedance of each of the plural electrodes, and a processor configured to control a contact impedance by the plural electrodes by generating the control signal to control at least one of plural switches connected respectively to the plural electrodes, or variable resistors connected respectively to the plural electrodes, based on at least one of a selectively set purpose of the plural electrodes or a position of an electrode to which nerve stimulation is to be provided.

20 Claims, 13 Drawing Sheets

(58) Field of Classification Search
CPC ............ A61N 1/36125; A61N 1/36146; A61N 1/36153; A61B 5/40; A61B 5/686; A61B 5/294; A61B 5/388; A61B 2560/0266
See application file for complete search history.

(56) References Cited

U.S. PATENT DOCUMENTS

| | | | |
|---|---|---|---|
| 2006/0149337 A1 | 7/2006 | John | |
| 2007/0021814 A1* | 1/2007 | Inman | A61N 1/36142 |
| | | | 607/141 |
| 2007/0100391 A1* | 5/2007 | Armstrong | A61N 1/37264 |
| | | | 607/45 |
| 2010/0114258 A1* | 5/2010 | Donofrio | A61N 1/39624 |
| | | | 607/2 |
| 2010/0125315 A1* | 5/2010 | Parramon | A61N 1/36157 |
| | | | 607/2 |
| 2015/0306393 A1* | 10/2015 | Groenland | A61N 1/0534 |
| | | | 607/116 |
| 2016/0008602 A1* | 1/2016 | Perryman | A61N 1/37223 |
| | | | 607/61 |
| 2016/0354010 A1 | 12/2016 | Hauck et al. | |
| 2017/0001003 A1* | 1/2017 | Pivonka | A61B 5/6871 |
| 2018/0092560 A1 | 4/2018 | Holder et al. | |
| 2018/0185651 A1 | 7/2018 | Astrom et al. | |
| 2020/0368534 A1* | 11/2020 | Nassif | A61N 1/36175 |

FOREIGN PATENT DOCUMENTS

| | | |
|---|---|---|
| KR | 10-2019-0078678 A | 7/2019 |
| KR | 10-2058372 B1 | 12/2019 |
| KR | 10-2020-0073974 A | 6/2020 |

\* cited by examiner

IMPLANT SYSTEM AND METHOD

CROSS-REFERENCE TO RELATED APPLICATIONS

This application claims the benefit under 35 U.S.C. § 119(e) of U.S. Provisional Application No. 63/126,639 filed on Dec. 17, 2020, in the U.S. Patent and Trademark Office, the entire disclosure of which is incorporated herein by reference for all purposes.

BACKGROUND

1. Field

The following description relates to an implant system and an operating method of the implant system.

2. Description of Related Art

An implant device implanted into a body of a user may typically have had a sensing function and a stimulating function for treating an extremely limited volume (e.g., 1 cc to 30 cc). The implant device may also support a wireless communication function for wireless communication with an external device for simple control. In a case in which the implant device uses a plurality of electrodes for stimulation, an impedance mismatch may occur among the electrodes.

SUMMARY

This Summary is provided to introduce a selection of concepts in a simplified form that is further described below in the Detailed Description. This Summary is not intended to identify key features or essential features of the claimed subject matter, nor is it intended to be used as an aid in determining the scope of the claimed subject matter.

In one general aspect, an implant system includes an electrode portion including plural electrodes to perform nerve stimulation and nerve sensing, an impedance controller configured to selectively connect the plural electrodes between a stimulator to perform nerve stimulation and a sensor to perform nerve sensing based on a control signal, and set an impedance of each of the plural electrodes, and a processor configured to control a contact impedance by the plural electrodes by generating the control signal to control at least one of plural switches connected respectively to the plural electrodes, or variable resistors connected respectively to the plural electrodes, based on at least one of a selectively set purpose of the plural electrodes or a position of an electrode to which nerve stimulation is to be provided.

The processor may be configured to generate the control signal to control a position of a target electrode to which nerve stimulation is to be provided based on the set purpose of use of the plural electrodes, the number of target electrodes, and a setting value of a variable resistor connected to the target electrode, based on the set purpose of use of the plural electrodes.

The processor may be configured to determine whether to group the plural electrodes based on the set purpose of use of the plural electrodes, and generate the control signal to selectively control the switches to connect the plural electrodes between the sensor and the stimulator based on the set purpose, including the processor being configured to generate the control signal to control the switches to connect the plural electrodes to the sensor when the set purpose of use of the plural electrodes is to perform sensing, and configured to alternately generate the control signal to control the switches to connect the plural electrodes to the stimulator when the set purpose of use of the plural electrodes is to perform stimulation.

The processor may be configured to determine whether to group the plural electrodes, or to group a portion of the plural electrodes, based on at least one of the set purpose of use of the plural electrodes, a position to which nerve stimulation is to be provided based on the set purpose, or a direction in which nerve stimulation is to be provided.

For when the set purpose of use of the plural electrodes is to perform nerve stimulation, the processor may be configured to group at least a portion of the plural electrodes into one channel, and generate the control signal for the variable resistors respectively connected to the plural electrodes such that a contact impedance by the grouped electrodes stimulates a target stimulation portion.

For when the set purpose of use of the electrodes is to perform nerve stimulation, the processor may be configured to generate the control signal to control an electrode impedance of each of plural target electrodes corresponding to a portion of a nerve among the plural electrodes to control a current amount of the plural target electrodes.

For when the set purpose of use of the plural electrodes is to perform nerve sensing, the processor may be configured to generate the control signal for the variable resistors respectively connected to the plural electrodes to allow current values flowing in channels respectively corresponding to the plural electrodes to be equal.

The processor may be configured to provide nerve stimulation by obtaining an impedance of each of the plural electrodes through the sensor and controlling a variable resistor for each of the plural electrodes based on the impedance of each of the plural electrodes.

The processor may be configured to control at least one of the switches or the variable resistors by generating the control signal based on a time set by a timer.

The impedance controller may include a plurality of sensors each configured to sense an electrode impedance of each of the plural electrodes, the variable resistors each configured to control the electrode impedance of each of the plural electrodes, and the switches each configured to selectively connect each of the plural electrodes between the stimulator and the sensor.

The sensor may be configured to perform nerve sensing by measuring a voltage level through the plural electrodes and the switches.

The stimulator may be configured to perform nerve stimulation by providing an electrical signal to an electrode among the plural electrodes through the switches.

The electrode portion may include an electrode array including the plural electrodes.

In one general aspect, an implant method may include obtaining impedance information of each of plural electrodes of the implant system, determining a variable resistance value for each of the plural electrodes based on a stimulation pattern predefined according to a selectively set purpose of use of the plural electrodes, using the impedance information of each of the plural electrodes, generating a control signal for controlling each of switches and variable resistors respectively connected to the plural electrodes based on the variable resistance value for each of the plural electrodes, and providing a stimulation pulse to a stimulation portion based on the stimulation pattern by controlling a contact impedance by the plural electrodes, based on the control signal.

The determining of the variable resistance value for each of the plural electrodes may include determining a variable resistance value for each of the plural electrodes including target electrodes corresponding to the stimulation portion based on the stimulation pattern, based on the impedance information of each of the plural electrodes and the target electrodes.

The generating of the control signal may include generating the control signal to control each of the switches and the variable resistors respectively connected to the plural electrodes based on the variable resistance value for each of the plural electrodes, using at least one of the set purpose of use of the plural electrodes or a position of an electrode to which nerve stimulation is to be provided.

The method may include the set purpose of use of the electrodes being to perform nerve stimulation, where the generating of the control signal may include grouping at least a portion of the plural electrodes into one channel, and generating the control signal for the variable resistors respectively connected to the plural electrodes such that a contact impedance by the grouped electrodes stimulates a target stimulation portion.

The method may include the set purpose of use of the electrodes being to perform nerve sensing, where the generating of the control signal may include generating the control signal for the variable resistors respectively connected to the plural electrodes such that current values flowing in channels respectively corresponding to the plural electrodes are to be equal.

The method may further include setting a timer based on a time set based on a sensing period of the impedance information of each of the plural electrodes and a stimulation period of the stimulation pulse, where the generating of the control signal includes generating the control signal for controlling each of the switches and the variable resistors respectively connected to the plural electrodes based on a time set by the timer.

In one general aspect, a non-transitory computer-readable storage medium stores instructions that, when executed by a processor, cause the processor to perform any one or any combination or all operations or methods described herein.

Other features and aspects will be apparent from the following detailed description, the drawings, and the claims.

BRIEF DESCRIPTION OF THE DRAWINGS

Throughout the drawings and the detailed description, the same reference numerals refer to the same or like elements. The drawings may not be to scale, and the relative size, proportions, and depiction of elements in the drawings may be exaggerated for clarity, illustration, and convenience.

DETAILED DESCRIPTION

Figure 1:
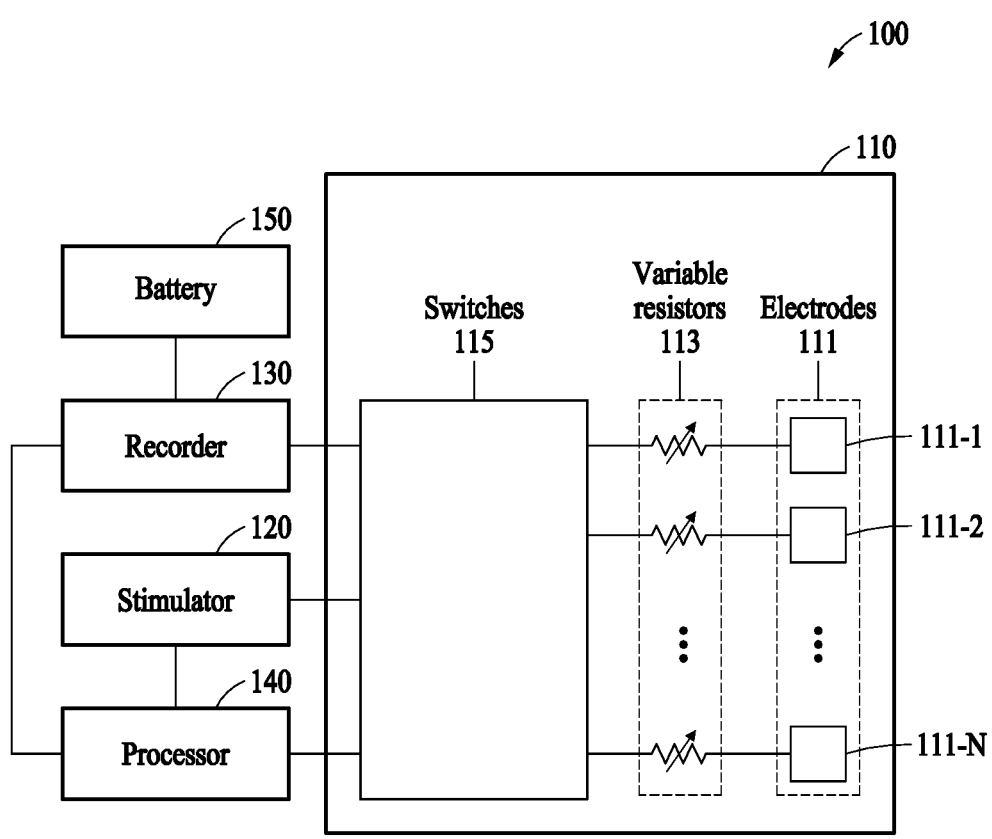
FIG. 1 illustrates an example of an implant system.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, some descriptions of features that are known after an understanding of the disclosure of this application may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The terminology used herein is for the purpose of describing particular examples only, and is not to be used to limit the disclosure. As used herein, the singular forms "a," "an," and "the" are intended to include the plural forms as well, unless the context clearly indicates otherwise. As used herein, the term "and/or" includes any one and any combination of any two or more of the associated listed items. As used herein, the terms "include," "comprise," and "have" specify the presence of stated features, numbers, operations, elements, components, and/or combinations thereof, but do not preclude the presence or addition of one or more other features, numbers, operations, elements, components, and/or combinations thereof. The use of the term "may" herein with respect to an example or embodiment (e.g., as to what an example or embodiment may include or implement) means that at least one example or embodiment exists where such a feature is included or implemented, while all examples are not limited thereto.

In addition, terms such as first, second, A, B, (a), (b), and the like may be used herein to describe components. Each of these terminologies is not used to define an essence, order, or sequence of a corresponding component but used merely to distinguish the corresponding component from other component(s). As another example, although terms of "first" or "second" may be used to explain various components, the components are not limited to the terms. These terms should be used only to distinguish one component from another component. For example, a "first" component may be referred to as a "second" component, or similarly, and the "second" component may be referred to as the "first" component within the scope of the right according to the concept of the present disclosure.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween. Likewise, expressions, for example, "between" and "immediately between" and "adjacent to" and "immediately adjacent to" may also be construed as described in the foregoing.

Unless otherwise defined, all terms, including technical and scientific terms, used herein have the same meaning as commonly understood by one of ordinary skill in the art to which this disclosure pertains consistent with and after an understanding of the present disclosure. Terms, such as those defined in commonly used dictionaries, are to be interpreted as having a meaning that is consistent with their meaning in the context of the relevant art and the present disclosure, and are not to be interpreted in an idealized or overly formal sense unless expressly so defined herein.

FIG. 1 illustrates an example of an implant system. Referring to FIG. 1, an implant system 100 may include an impedance controller 110 including an electrode portion 111, a stimulator 120, a recorder 130, a processor 140, and a battery 150, for example.

The impedance controller 110 may control the connection of a plurality of electrodes 111-1, 111-2, . . . , and 111-N of the electrode portion 111 between the stimulator 120 to perform nerve stimulation and to the recorder 130 to perform nerve sensing based on a control signal of the processor 140, and set an impedance for each of the electrodes. The impedance for each electrode may also be referred to herein as an electrode impedance as it indicates an impedance of an individual electrode. The control signal may be determined based on, for example, an electrode impedance sensed for each electrode. For example, in one example the control signal is a signal for setting resistance values of variable resistors 113 included in the impedance controller 110, and/or for controlling an operation of switches 115.

Figure 10:
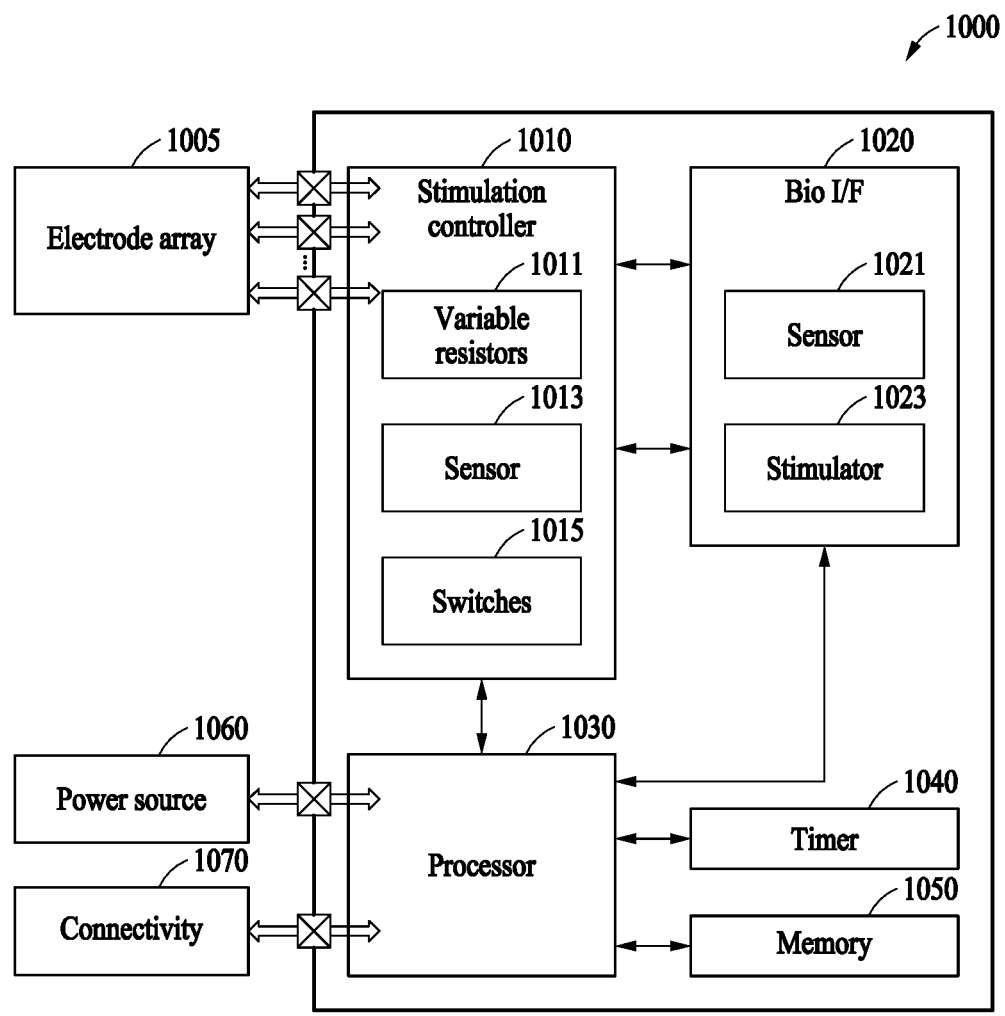
FIG. 10 illustrates an example of a configuration of an implant system.

The impedance controller 110 may include the variable resistors 113 and the switches 115, in addition to the electrode portion 111. The electrode portion 111 may be included in the impedance controller 110 as illustrated in FIG. 1, or be separate from the impedance controller 110, such as illustrated in FIG. 10, as a non-limiting example.

Figure 2:
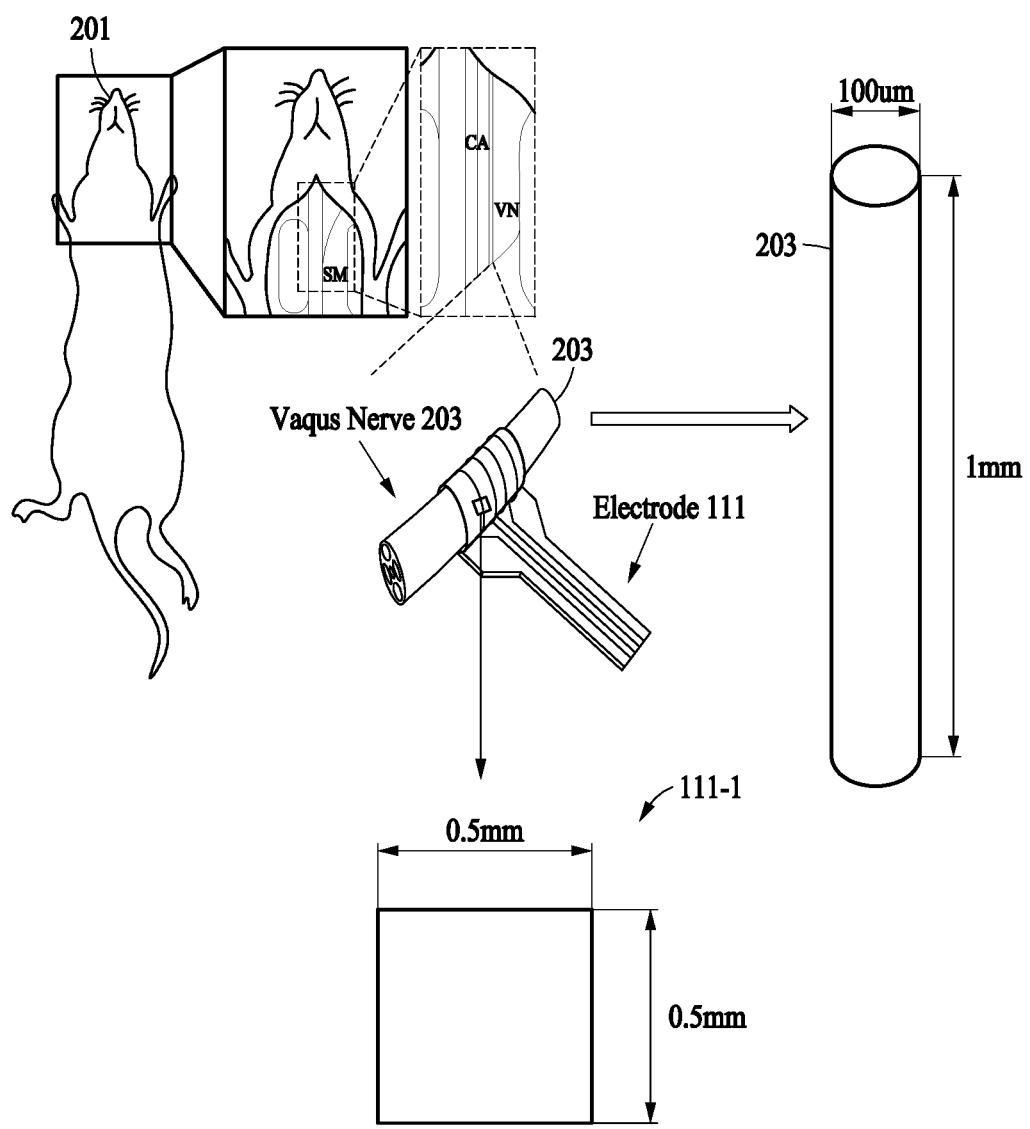
FIG. 2 illustrates an example of electrodes of an implant system being combined with a vagus nerve of a test object.

The electrode portion 111 may include the electrodes 111-1, 111-2, . . . , and 111-N available for nerve stimulation and nerve sensing. The electrode portion 111 may be embodied as, for example, an electrode array including the electrodes 111-1, 111-2, . . . , and 111-N, but is not limited thereto. The electrodes 111-1, 111-2, . . . , and 111-N included in the electrode portion 111 may also be referred to herein as implant electrodes in that they are combined with a target nerve and when implanted to provide stimulation, as illustrated in FIG. 2. Thus, references to either of the electrode(s) or the implant (or implanted) electrode(s) should also be construed as a reference to the other.

The electrodes 111-1, 111-2, . . . , and 111-N included in the electrode portion 111 may not be divided dependent on their use in, for example, nerve stimulation or nerve sensing, but may be used for both nerve stimulation and nerve sensing. The electrodes 111-1, 111-2, . . . , and 111-N may be, for example, electrodes to perform nerve sensing with a relatively high contact impedance.

In an example, when the set/selected purpose use of the electrodes is to perform nerve stimulation, the electrodes 111-1, 111-2, . . . , and 111-N may be used by being grouped into at least one channel. When the set/selected purpose of the electrodes is to perform nerve sensing, the electrodes 111-1, 111-2, . . . , and 111-N may be used for channels respectively corresponding to the electrodes 111-1, 111-2, . . . , and 111-N. Here, the set (i.e., controlled) purpose is a selectively set purpose, as the set purpose of use of the electrodes may be controlled to change between a set purpose of use of the electrodes being to perform stimulation, and a set purpose of use of the electrodes being to perform sensing, as non-limiting examples.

For example, when electrodes are controlled to perform nerve stimulation, a relatively low level of a contact impedance may be used. A current value for nerve stimulation may be determined based on a relationship between an input voltage and a contact impedance of the electrodes. This is because, as the contact impedance of the electrodes increases, a higher voltage may be used to meet the current value for nerve stimulation. For the implant system 100, a level of an input voltage may be extremely low, and thus a low contact impedance value (e.g., kiloohms kΩ) the electrodes may be used. In general, the contact impedance of the electrodes may be inversely proportional to the size of the electrodes. Thus, for a low level of a contact impedance, the size of the electrodes may not be less than a certain level, as only as an example.

However, when electrodes are set or controlled to perform nerve sensing, examples include the electrodes having a few kf) of a contact impedance, and thus in such an example the electrodes may be smaller in size than electrodes for nerve stimulation.

In an example, both nerve sensing and stimulation may be performed on a target nerve in a small space by using electrodes configured for nerve sensing, without separate electrodes for nerve stimulation. That is, the electrode portion 111 may include a plurality of electrodes configured to perform sensing, but may not separately include electrodes for only stimulation. Instead, for nerve stimulation, the electrodes configured to perform sensing may be selectively grouped through the switches 115 to become connected in parallel, and then the grouped electrodes may be thereby configured to perform stimulation. Here, each of the grouped electrodes may be connected in parallel, and it is thus possible in varied examples to reduce a contact impedance in inverse proportion to the number of the parallel-connected electrodes. Thus, a contact impedance may be met for an electrode to perform stimulation.

Rather, in a case in which a plurality of electrodes for stimulation are grouped and the grouped electrodes are used for sensing, a contact impedance of each of the electrodes may differ from each other, and thus a uniform current value may not be achieved. When such an impedance mismatch increases, a difference in terms of current values flowing in the electrodes may increase. Thus, one or more example implant systems herein, e.g., the implant system 100, may address such impedance mismatches that may occur when using the grouped electrodes to perform stimulation, by controlling a current amount of each of the electrodes through variable resistors and switches to provide the intended/set stimulation.

The implant system 100 may verify an impedance mismatch that may occur when grouping electrodes to perform stimulation through the recorder 130, and may thus address the impedance mismatch by controlling a resistance value of the variable resistors 113. The implant system 100 may concentrate a current in a certain direction by relatively maximizing a current amount of an electrode to provide stimulation to a certain portion. In addition, the implant system 100 may control the switches 115 to connect the electrodes 111-1, 111-2, . . . , and 111-N to the stimulator 120 and the recorder 130.

By reducing the size of electrodes to be used to perform stimulation and providing the electrodes with the example reduced sizes to the implant system 100, the implant system 100 may control the electrodes to perform various set/controlled purposes in addition to the selective setting/controlling of a purpose only between performing stimulation and sensing.

The electrodes included in the electrode portion 111 may be connected to a bio-interface for nerve stimulation or sensing. Although to be described hereinafter, the bio-interface may include the stimulator 120 configured to provide nerve stimulation and the recorder 130 configured to record nerve sensing. The connection between the bio-interface including the stimulator 120 and the recorder 130 and the electrodes 111-1, 111-2, . . . , and 111-N of the electrode portion 111 may be controlled through the switches 115. The switches 115 may be controlled by the processor 140. By a control signal for the switches 115, the electrodes 111-1, 111-2, . . . , and 111-N may be selectively connected to the stimulator 120 or the recorder 130.

The variable resistors 113 may control an electrode impedance of each of the electrodes 111-1, 111-2, . . . , and 111-N.

The switches 115 may connect each of the electrodes 111-1, 111-2, . . . , and 111-N to the stimulator 120 or the recorder 130.

The stimulator 120 may perform nerve stimulation by providing an electrical signal to an electrode among the electrodes 111-1, 111-2, . . . , and 111-N through the switches 115.

The recorder 130 may include sensors configured to sense an electrode impedance of each of the electrodes 111-1, 111-2, . . . , and 111-N. The recorder 130 may perform nerve sensing by measuring a voltage level through the electrodes 111-1, 111-2, . . . , and 111-N and the switches 115. The recorder 130 may also be referred to herein as a sensor or a sensing portion in that it performs nerve sensing. Hereinafter, terms "recorder," "recording portion, "sensor," and "sensing portion" may be used interchangeably. The stimulator 120 and the recorder 130 may be included in the bio-interface to be described hereinafter with reference to FIG. 10.

The processor 140 may control a contact impedance by electrodes by generating a control signal for controlling at least one of the switches 115 respectively connected to the electrodes 111-1, 111-2, . . . , and 111-N and the variable resistors 113 respectively connected to the electrodes 111-1, 111-2, . . . , and 111-N, based on at least one of a set (i.e., controlled, or user controlled) purpose of use of the electrodes 111-1, 111-2, . . . , and 111-N or a position of an electrode to which nerve stimulation is to be provided.

The processor 140 may generate a control signal for controlling a position of a target electrode(s) for providing nerve stimulation according to the purpose of use, the number of target electrodes, and a setting value (e.g., a resistance value) of a variable resistor(s) connected to the target electrode(s), based on the purpose of use of the electrodes 111-1, 111-2, . . . , and 111-N.

The processor 140 may determine whether to group the electrodes 111-1, 111-2, . . . , and 111-N based on the set purpose of use of the electrodes 111-1, 111-2, . . . , and 111-N. The processor 140 may generate a control signal for selectively controlling the switches 115 to connect the electrodes 111-1, 111-2, . . . , and 111-N between the stimulator 120 and the recorder 130, based on whether to group the electrodes 111-1, 111-2, . . . , and 111-N.

The processor 140 may determine whether to group the electrodes 111-1, 111-2, . . . , and 111-N and determine electrodes to be grouped among the electrodes 111-1, 111-2, . . . , and 111-N, based on at least one of the set purpose of use of electrodes, a position to which nerve stimulation is to be provided based on the purpose of the electrodes, or a direction in which nerve stimulation is to be provided.

For example, in a case in which the set purpose of use of the electrodes 111-1, 111-2, . . . , and 111-N is for nerve stimulation, the processor 140 may group at least a portion of the electrodes 111-1, 111-2, . . . , and 111-N into one channel. The processor 140 may generate a control signal for variable resistors for the electrodes such that a contact impedance by the grouped electrodes is inversely proportional to the number of the grouped electrodes. Also, in a case in which the set purpose of use of the electrodes 111-1, 111-2, . . . , and 111-N is for nerve stimulation, the processor 140 may generate a control signal for controlling an electrode impedance of each target electrode to control a current amount of target electrodes corresponding to a predetermined portion of a nerve among the electrodes 111-1, 111-2, . . . , and 111-N.

For another example, in a case in which the set purpose of use of the electrodes 111-1, 111-2, . . . , and 111-N is for nerve sensing, the processor 140 may generate a control signal for variable resistors respectively connected to the electrodes 111-1, 111-2, . . . , and 111-N such that current values flowing in channels respectively corresponding to the electrodes 111-1, 111-2, . . . , and 111-N are to be equal.

The processor 140 may obtain an impedance of each of the electrodes 111-1, 111-2, . . . , and 111-N through the recorder 130. The processor 140 may provide nerve stimulation by controlling a variable resistor for each of the electrodes 111-1, 111-2, . . . , and 111-N based on the impedance obtained for each of the electrodes 111-1, 111-2, . . . , and 111-N. Nerve stimulation may be provided through a monophasic method or a biphasic method, for example.

Through the monophasic method, a flow of a current for providing nerve stimulation may be provided in one direction because a waveform has only one polarity. In a case in which nerve stimulation is provided through the monophasic method, the processor 140 may group all the electrodes 111-1, 111-2, . . . , and 111-N into one channel through a control signal for the switches 115. The grouped electrodes may be used to provide a stimulation waveform having one polarity.

Through the biphasic method, a flow of a current for providing nerve stimulation may be provided alternately in both directions (a direction and its opposite direction) because a waveform has two polarities. In a case in which nerve stimulation is provided through the biphasic method, the processor 140 may provide the same energy without increasing the energy.

As described above, in a case in which nerve stimulation is provided through the biphasic method, the processor 140 may group the electrodes 111-1, 111-2, . . . , and 111-N into two channels through a control signal for the switches 115.

The electrodes grouped into the two channels may be used to provide stimulation waveforms having two polarities. One of the two channels may operate as a working electrode, and the other of the two channels may operate as a counter electrode.

In another example, the implant system 100 may further include a timer (e.g., a timer 1050 of FIG. 10). In such an example, the processor 140 may generate a control signal based on a time set by the timer, and control at least one of the switches 115 or the variable resistors 113.

In an example, the implant system 100 may uniformly match respective impedances of the electrodes 111-1, 111-2, . . . , and 111-N, or concentrate a direction of stimulation in a predetermined portion by using an impedance mismatch among the electrodes 111-1, 111-2, . . . , and 111-N.

FIG. 2 illustrates an example of how electrodes of an implant system are combined with a vagus nerve of a test object. Referring to FIG. 2, of a carotid artery (CA) and a vagus nerve (VN) 203 included in a sternocephalic muscle (SM) of a test object 201, an electrode portion 111 is combined with the VN 203. In the example of FIG. 2, the VN 203 may have a diameter of 100 micrometers (µm) and a length of 1 millimeter (mm).

For example, a contact impedance of an electrode for nerve sensing may be allowed up to hundreds of kΩ, whereas a contact impedance of an electrode for nerve stimulation may be allowed up to a few kΩ. A contact impedance of an electrode increases as the size of the electrode decreases. Thus, to meet the contact impedance of the electrode for nerve stimulation, the size of the electrode may need to be greater than a certain size. Thus, it may not be easy to apply an electrode having a size greater than a certain level to a small implant system limited in size.

An implant system may perform stimulation and multi-channel sensing to operate in a closed-loop, and thus a multi-channel electrode to perform sensing may be used. To the electrode portion 111 to perform nerve stimulation, an impedance of a few kΩ may be provided due to a compliance voltage. The compliance voltage represents an output voltage in a constant current mode of a direct current (DC) source, and a range of an output voltage used to maintain a constant load current may be referred to as a compliance range.

A stimulation pulse provided through the electrode portion 111 may be hundreds of microamperes (µA), and a stimulation voltage may be 10 to 20 voltages (V). The electrode portion 111 may include cuff electrodes, for example. For example, an electrode 111-1 included in the electrode portion 111 may be in a form of a square with a width of 0.5 mm and a length of 0.5 mm, but is not limited thereto. The electrode 111-1 may have a size used to have a few kΩ level of a contact impedance that is used to meet a corresponding stimulation current level.

Figure 3A:
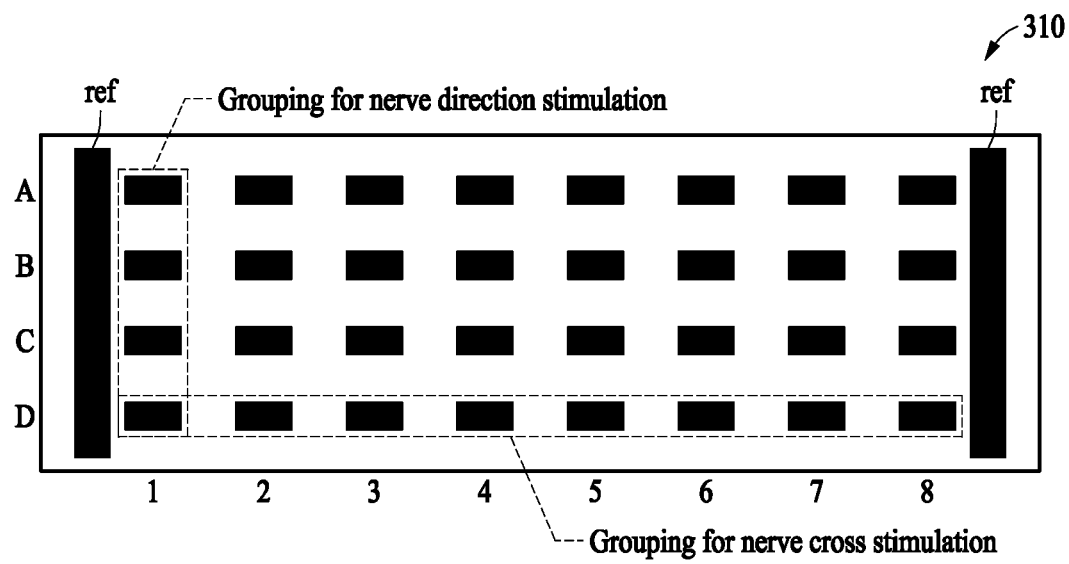
FIGS. 3A, 3B, and 3C illustrate an example of an electrode array including electrodes.
Figure 3B:
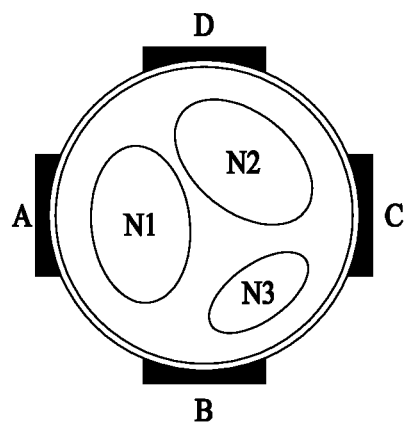
Figure 3C:
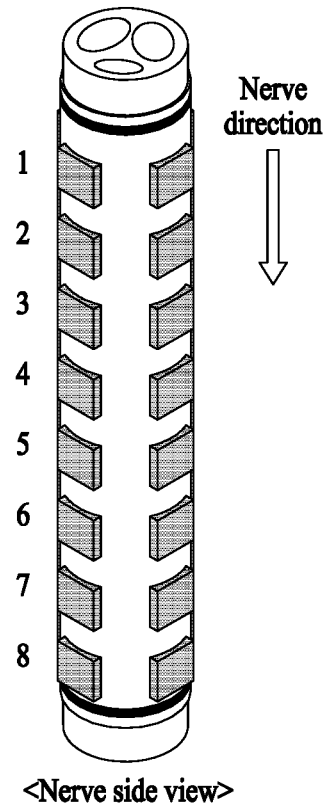

FIGS. 3A, 3B, and 3C illustrate an example of an electrode array including electrodes. FIG. 3A is a diagram illustrating an example of an electrode array 310, FIG. 3B is a cross-sectional view of a nerve ganglion combined with the electrode array 310, and FIG. 3C is a side view of the nerve ganglion combined with the electrode array 310.

An implant system may diversify a stimulation pattern and/or a stimulation portion by increasing the number of electrodes and grouping the increased number of electrodes in various ways. The implant system may group the electrodes in various forms based on a stimulation portion of a nerve to be stimulated and/or a stimulation direction. For example, varied examples of the implant system may group electrodes in a vertical direction of the electrode array 310 to perform stimulation in a nerve direction (or simply nerve direction stimulation). Alternatively, or in addition, varied examples of the implant system may group electrodes in a horizontal direction of the electrode array 310 to perform stimulation in a direction crossing a nerve (or simply nerve cross stimulation). The implant system may group electrodes in various ways based on the direction in which nerve stimulation is to be provided. The direction in which nerve stimulation is configured to be provided may simply be referred to herein as a stimulation direction.

For example, the implant system may stimulate a nerve (e.g., N3) illustrated in FIG. 3B.

Figure 11:
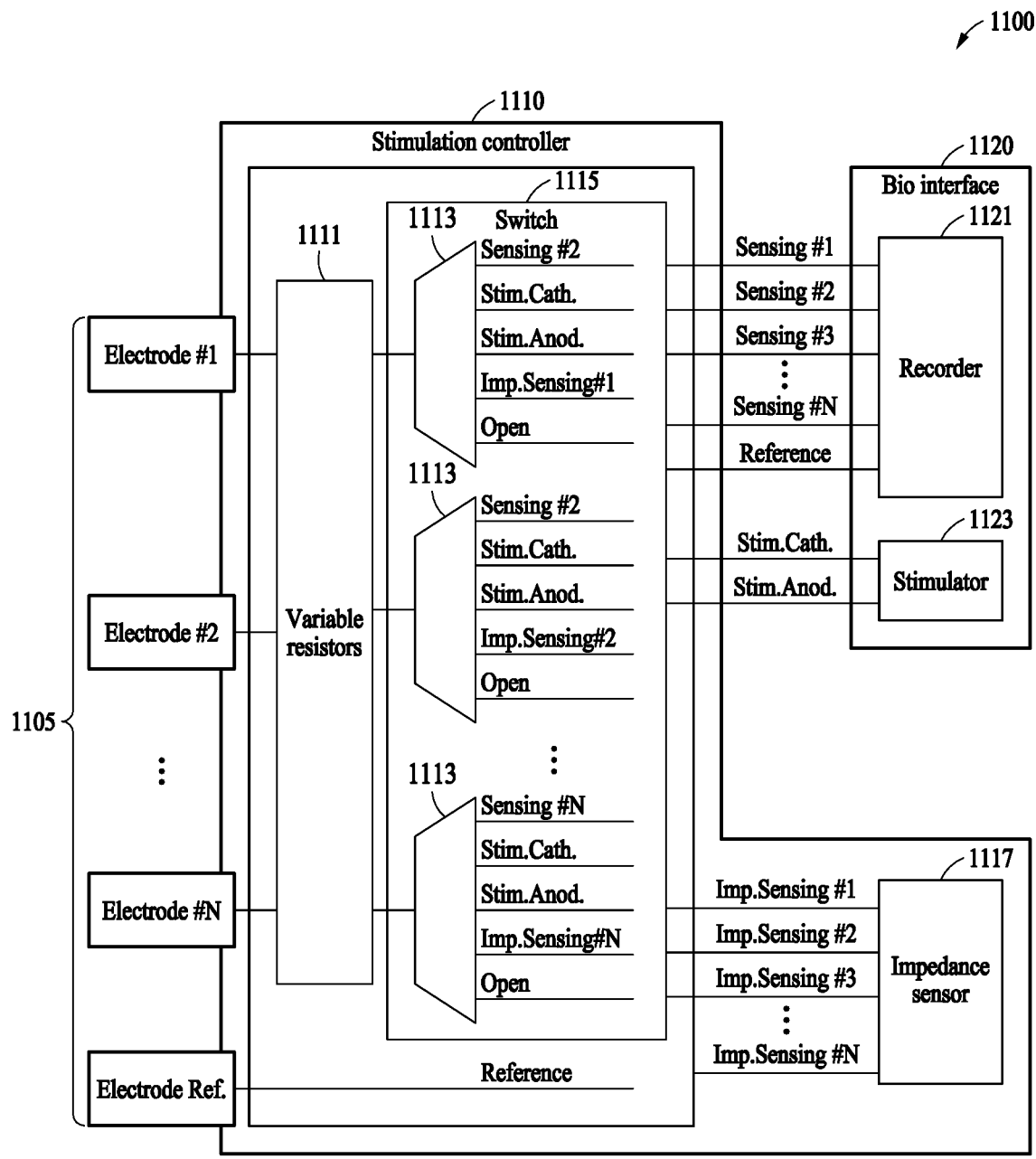
FIG. 11 illustrates an example of a detailed configuration of the implant system of FIG. 10.

In this example, the implant system may group eight electrodes corresponding to electrode B and 8 electrodes corresponding to electrode C in a horizontal direction of the electrode array 310. The implant system may connect the grouped 16 electrodes to a cathode electrode and an anode electrode of a stimulator as illustrated in FIG. 11, for example, to provide nerve stimulation. Also, the implant system may group four electrodes or more neighboring electrodes each in a vertical direction of the electrode array 310, and connect the grouped electrodes to the cathode electrode and the anode electrode of the stimulator to provide additional nerve stimulation in a nerve direction.

However, in the example of stimulating a certain nerve, for example, N3, there may be an issue of a compliance voltage that is used to satisfy a range of an output voltage used for maintaining a certain load current. Thus, when grouping electrode C and electrode D together, an issue of unequally concentrated stimulation may occur. Such a potential of unequally concentrated stimulation will be described in detail with reference to FIGS. 4A and 4B.

For example, when an impedance of electrode D is relatively lower than an impedance of electrode C, a current flowing from electrode B to electrode C may be relatively greater than a current flowing from electrode B to electrode D. A difference in a current amount flowing in each of electrodes may increase as an impedance mismatch increases.

The implant system may maintain impedances of electrodes to be at a similar level by using variable resistors, thereby preventing stimulation from being concentrated in an unintended direction.

Figure 6A:
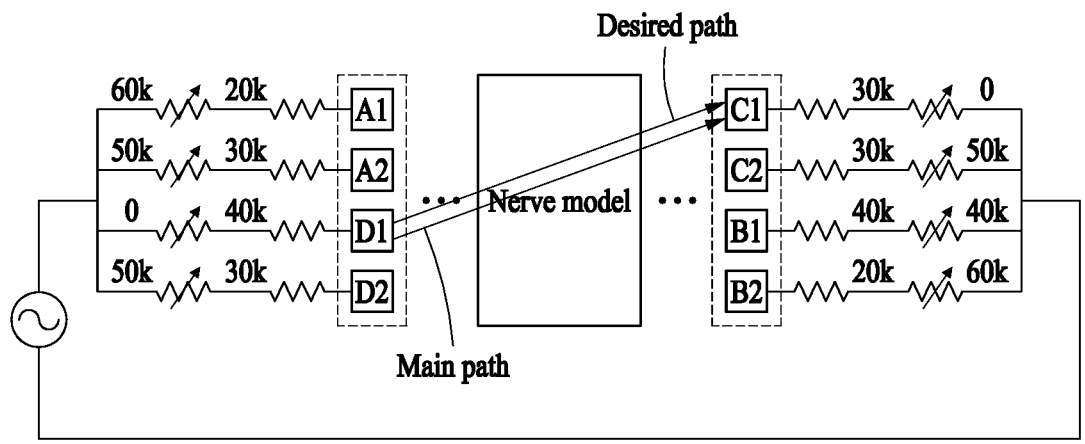
FIGS. 6A and 6B illustrate an example of setting a resistance value of a variable resistor to provide stimulation to a portion by an implant system.
Figure 6B:
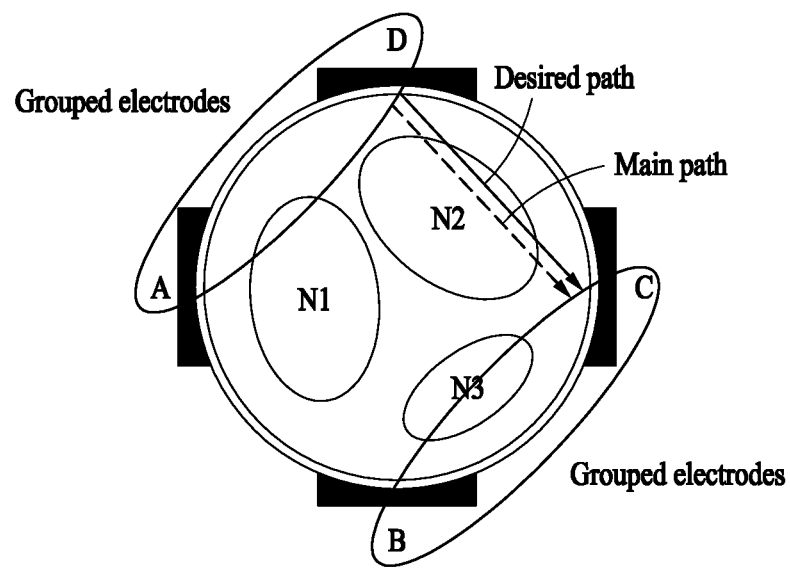

For example, by grouping electrodes in consideration of the compliance voltage, even though it is desired/intended, e.g., by a user or operator, to stimulate a nerve N2 from electrode D to electrode C, undesired electrode A and electrode B may be additionally grouped. In such an example, due to an impedance mismatch to be described hereinafter with reference to FIGS. 4A and 4B, a current flowing from electrode A to electrode B may be relatively greater than a current flowing from electrode D to electrode C. In this example, to minimize the amount of the current flowing from electrode A to electrode B, the implant system may increase an impedance using variable resistors on electrode A and electrode B sides as illustrated in FIGS. 6A and 6B, thereby allowing a stimulation waveform to be concentrated from electrode D to electrode C as desired/intended.

Examples of setting resistance values of variable resistors by the implant system to provide stimulation to a certain portion (e.g., N3) will be described in detail with reference to FIGS. 5, 6A, and 6B. Also, an example of setting resistance values of variable resistors by the implant system to address an impedance mismatch that may occur among a plurality of electrodes will be described in detail with reference to FIG. 8.

Figure 4A:
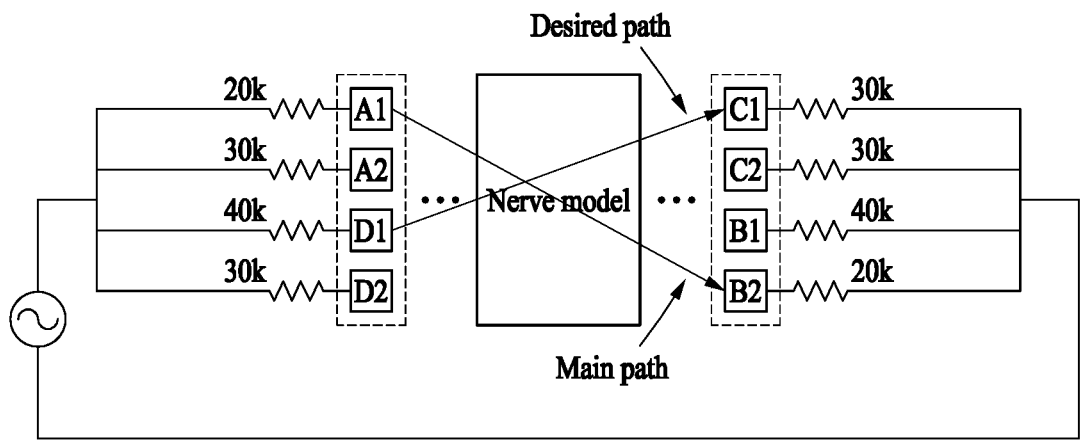
FIGS. 4A and 4B illustrate an example of a situation in which stimulation is concentrated on some of electrodes grouped for nerve stimulation.
Figure 4B:
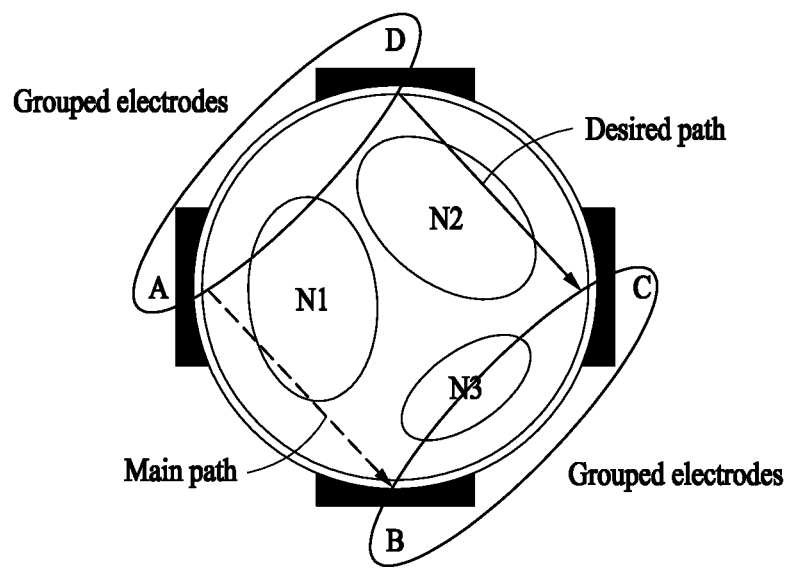

FIGS. 4A and 4B illustrate an example of a situation in which stimulation is concentrated on some of electrodes grouped to perform nerve stimulation.

An electrode to perform nerve stimulation has a contact impedance that is be less than or equal to 1 kΩ, for example, and thus the size of the electrode may be greater than a predetermined size, e.g., to satisfy the contact impedance, the electrode may have a size greater than the predetermined size. In addition, due to a limited size, the number of electrodes to perform stimulation to be provided in an implant system of a small size corresponding to a few cc may also be limited. For such reasons, when providing, in the implant system, electrodes having a contact impedance suitable for the set purpose, the number of the electrodes may be limited based on the set purpose of use.

In an example, to address such an issue of the number of electrodes limited according to the set purpose of use, in one or more examples a plurality of electrodes configured to perform sensing (or sensing electrodes) may be grouped together to be used as electrodes to perform stimulation (or as stimulation electrodes). However, in such an example of using the grouped sensing electrodes, an impedance mismatch may occur for each of the electrodes, and thus a deviation in the current amount flowing in each of the electrodes may occur. When the impedance mismatch among the electrodes increases, the deviation in the current amount may increase and a current may be directed in an unpredicted direction.

FIG. 4A illustrates an example where stimulation is concentrated in an unintended direction by grouped electrodes when a target stimulation direction is set from electrode D1 to electrode C1. FIG. 4B illustrates an example where nerve stimulation is not provided through a desired path but through an unintended path, and thus a certain nerve (e.g., N2) is not stimulated as intended.

For example, a target stimulation direction of stimulating a nerve (e.g., N2) illustrated in FIG. 4B may be set to be a direction from electrode D1 to electrode C1 as illustrated in FIG. 4A. In this example, due to an impedance of the electrodes, electrode A and electrode B may also be used to group electrode A and electrode D into a single channel, and electrode B and electrode C into another channel. Each electrode may include two sub-electrodes—a cathode electrode and an anode electrode.

A total impedance of electrode D may be 17.4 kΩ by grouped (or parallel-connected) sub-electrode D1 (impedance 40 kΩ) and sub-electrode D2 (impedance 30 kΩ). Also, a total impedance of electrode C may be 15 kΩ by grouped (or parallel-connected) sub-electrode C1 (impedance 30 kΩ) and sub-electrode C2 (impedance 30 kΩ). Hereinafter, grouped electrodes may be construed as being the same as electrodes connected in parallel unless otherwise indicated.

In addition, a total impedance of electrode A that neighbors electrode D may be 12 kΩ by grouped sub-electrode A1 (impedance 20 kΩ) and sub-electrode A2 (impedance 30 kΩ). A total impedance of electrode B that neighbors electrode C may be 13.33 kΩ by grouped sub-electrode B1 (impedance 40 kΩ) and sub-electrode B2 (impedance 20 kΩ).

That is, even though a direction from electrode D toward electrode C is set as a desired/intended path for stimulation, a greater current may flow to electrode A having a lower impedance between electrode D and electrode A that are grouped into the one channel. Also, a current passing through electrode A may flow to electrode B having a lower impedance between electrode C and electrode B that are grouped together. Thus, as a current flows actually in an unintended direction from electrode A toward electrode B, the unintended direction may become a main path through which stimulation is transferred. As described above, due to an impedance mismatch between grouped electrodes, nerve stimulation may be concentrated in such a main path (e.g., the direction from electrode A toward electrode B), and not in a desired/intended path (e.g., the direction from electrode D toward electrode C).

Figure 5:
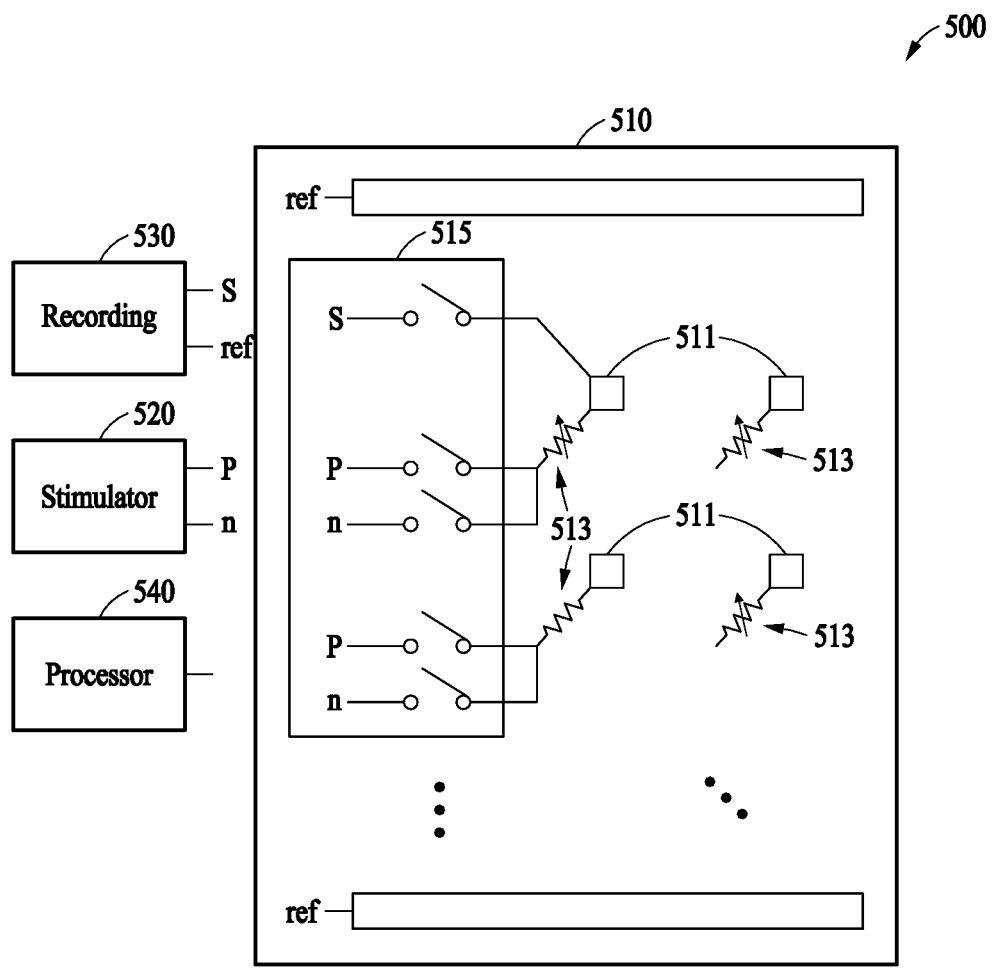
FIG. 5 illustrates an example of an operating method of an implant system.

FIG. 5 illustrates an example of an operating method of an implant system. Referring to FIG. 5, an implant system 500 may include an impedance controller 510 including electrodes 511, variable resistors 513, and switches 515, a stimulator 520, a recorder 530, and a processor 540.

The electrodes 511 may be electrically connected to one of a cathode electrode P of the simulator 520, an anode electrode N of the stimulator 520, and a sensing electrode S of the recorder 530. For example, the electrodes 511 may be electrically connected to one end of the variable resistors 513, and another end of the variable resistors 513 may be electrically connected to switches corresponding to the cathode electrode P of the stimulator 520 and the anode electrode N of the stimulator 520. In addition, the electrodes 511 may be electrically connected to switches corresponding to the sensing electrode S of the recorder 530.

Through such a circuit structure illustrated in FIG. 5, a portion of the electrodes 511 may be grouped to be electrically connected to the cathode electrode P of the stimulator 520, and a portion of the electrodes 511 may be grouped to be electrically connected to the anode electrode N. The grouped electrodes may be connected to the cathode electrode P or the anode electrode N of the stimulator 520 through variable resistors connected in parallel.

For example, in a case in which at least a portion of the electrodes 511 is connected to the sensing electrode S of the recorder 530, the recorder 530 may measure a potential difference between the portion of the electrodes 511 and a reference electrode (indicated as "ref" in FIG. 5).

FIGS. 6A and 6B illustrate an example of setting a resistance value of a variable resistor to provide stimulation to a portion by an implant system. FIG. 6A illustrates an example of setting resistance values of variable resistors respectively connected to electrodes to provide stimulation to a certain portion (e.g., N2) of a nerve. FIG. 6B illustrates an example situation in which nerve stimulation is provided to the nerve through a desired/intended path by the set resistance values of the variable resistors.

For example, in a case in which electrodes perform nerve stimulation, an example implant system may generate a control signal for variable resistors respectively connected to the electrodes such that a contact impedance by the grouped electrodes is inversely proportional to the number of the grouped electrodes. In this example, the control signal for the variable resistors may correspond to a signal setting resistance values of variable resistors respectively connected to electrodes.

The implant system may generate a control signal to control an electrode impedance for each target electrode to control a current amount of target electrodes corresponding to a certain portion (e.g., N2) of a nerve among electrodes. For example, the implant system may allow stimulation to be concentrated on a desired/intended path by controlling impedances of electrodes corresponding to a remaining path except for the desired/intended path using resistance values of corresponding variable resistors (or simply variable resistance values) while maintaining impedances of electrodes corresponding to the desired/intended path.

For example, each of electrodes providing nerve stimulation may have an impedance as illustrated in FIG. 4A, for example, A1 has 20 kΩ, A2 has 30 kΩ, D1 has 40 kΩ, D2 has 30 kΩ, C1 has 30 kΩ, C2 has 30 kΩ, B1 has 40 kΩ, and B2 has 20 kΩ.

In this example, the implant system may set respective resistance values of variable resistors respectively connected to the (sub)-electrodes A1, A2, D1, D2, C1, C2, B1, and B2 to be 60 kΩ, 50 kΩ, 0 kΩ, 50 kΩ, 0 kΩ, 50 kΩ, 40 kΩ, and 60 kΩ, respectively. By the variable resistors, the impedance of each of the sub-electrodes A1, A2, and D2 may be 80 kΩ. Also, the impedance of the sub-electrode D1 may be 40 kΩ. Also, the impedance of each of the sub-electrodes C2, B1, and B2 may be 80 kΩ. In addition, the impedance of the sub-electrode C1 may be 30 kΩ.

Thus, a total impedance of electrode A may be 40 kΩ. A total impedance of electrode D may be 26.67 kΩ. A total impedance of electrode C may be 21.81 kΩ. A total impedance of electrode B may be 40 kΩ.

As described above, the implant system may concentrate stimulation to be concentrated on a desired/intended direction (e.g., a direction from electrode D toward electrode C to stimulate the portion N2) as illustrated in FIG. 6B by setting a resistance value of a variable resistor to minimize an amount of stimulation flowing from electrode A or received by electrode B, that is, a current amount flowing in each electrode.

Figure 7A:
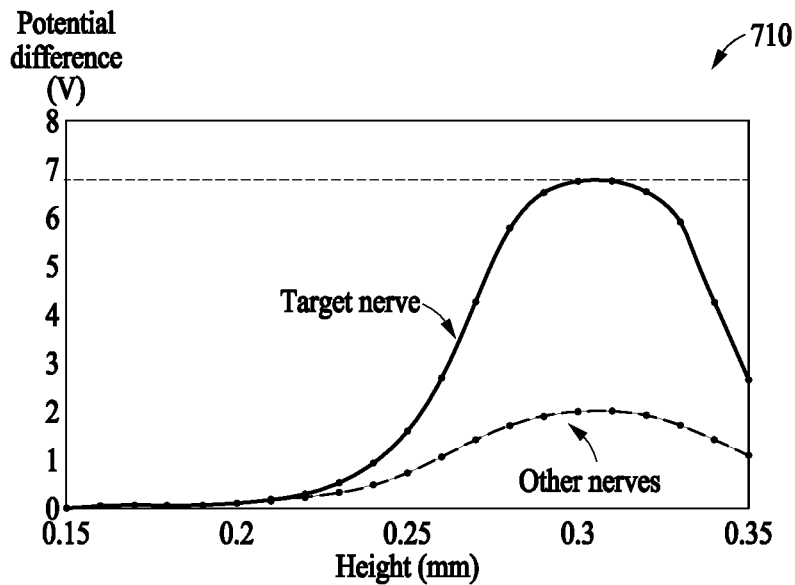
FIGS. 7A and 7B illustrate example graphs of a potential difference between a target nerve and other nerves by the resistance value set according to what is described with reference to FIGS. 6A and 6B.
Figure 7B:
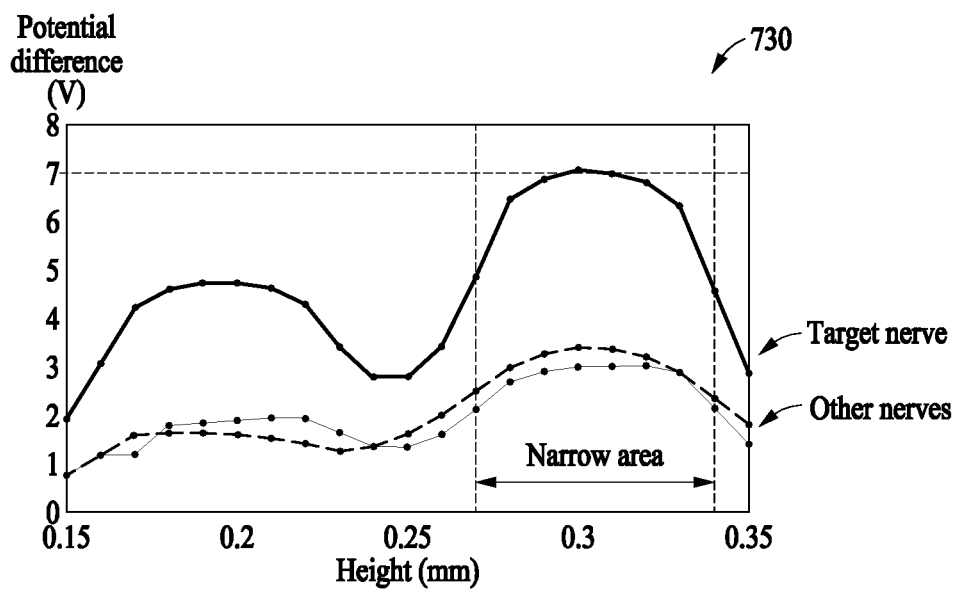

FIGS. 7A and 7B illustrate example graphs of a potential difference between a target nerve and other nerves by the resistance value set according to what is described with reference to FIGS. 6A and 6B. FIG. 7A illustrates a graph 710 indicating a result obtained by providing a voltage of 12V between electrode C1 (or a counter electrode) and electrode D1 (or a working electrode) corresponding to a target nerve (e.g., N2) with a height of 0.3 mm among eight electrodes A1, A2, B1, B2, C1, C2, D1, and D2 illustrated in FIG. 6A, providing a voltage of 0V to electrodes A1, A2, B1, B2, C2, and D2 corresponding to remaining nerves (e.g., N1 and N3), and comparing an end-to-end potential difference between the target nerve corresponding to electrode D1 and the other nerves corresponding to the other remaining electrodes A1, A2, B1, B2, C2, and D2. Here, a current corresponding to A may flow between electrodes D1 and C1.

Referring to the graph 710, by providing the voltage of 12V between electrodes C1 and D1 corresponding to the target nerve (e.g., N2) being in the height of 0.3 mm, a greater amount of a current may flow to the target nerve, than to the remaining nerves (e.g., N1 and N3), and thus stimulation may be provided to the target nerve.

FIG. 7B illustrates a graph 730 indicating a result obtained by providing a voltage of 12V to electrode D1 corresponding to a target nerve among four electrodes D1, D2, A1, and A2, respectively providing voltages of 8V, 2V, and 2V between remaining working electrodes D2, A1, and A2, and counter electrode groups B1, B2, C1, and C2, and comparing an end-to-end potential difference between the target nerve corresponding to electrode D1 and remaining nerves corresponding to the remaining electrodes. Here, a current of A may flow from electrode D1 to a counter electrode, and a current of A may additionally flow from the remaining electrodes D2, A1, and A2 to the counter electrode. Through this, it is possible to increase a current amount by controlling a current amount of working electrodes and concentrating on a target nerve.

Referring to the graph 730, it is observed that, in a case in which a voltage is provided to four electrodes D1, D2, A1, and A2, a potential difference corresponding to the target nerve being in the height of 0.3 mm is improved, compared to what is observed from the result indicated in the graph 710. As described above, a plurality of electrodes together, may concentrate stimulation on a target nerve (e.g., a stimulation portion) by increasing a potential difference for the target nerve without greatly increasing a potential difference of remaining nerves. In an example, without a variable resistor, such results may be reversed due to an impedance deviation between grouped electrodes, and thus an end-to-end potential difference of untargeted nerves (e.g., N1, N3) may be greater. The variable resistor may increase the potential difference for the target nerve and thus concentrate stimulation on the target nerve, thereby preventing the result from being reversed by the impedance deviation between the grouped electrodes.

Figure 8:
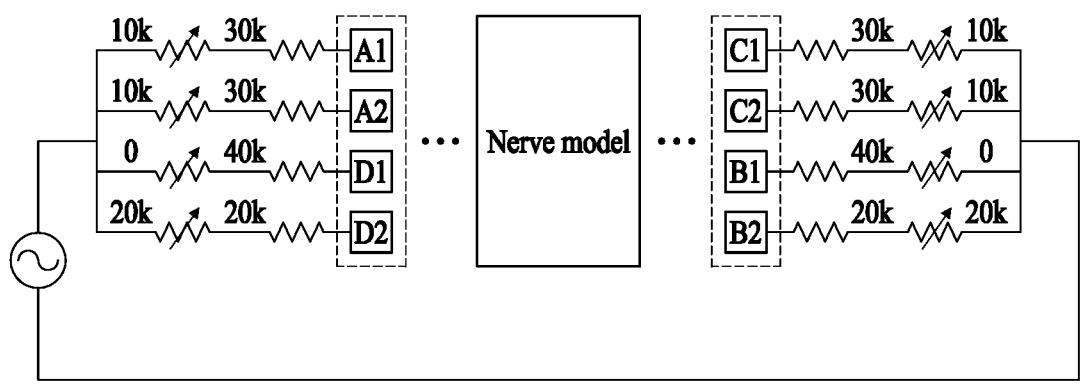
FIG. 8 illustrates an example of setting a resistance value of a variable resistor to remove an impedance mismatch occurring among a plurality of electrodes in an implant system.

FIG. 8 illustrates another example of setting a resistance value of a variable resistor for each electrode in an implant system. Referring to FIG. 8, in one or more examples, to address an impedance match that may occur among a plurality of grouped electrodes, a variable resistance value for each electrode may be set as described hereinafter.

For example, when the set purpose of electrodes is to perform impedance matching, e.g., rather than for concentrating stimulation at a certain position, an implant system may generate a control signal for variable resistors respectively connected to the electrodes such that current values flowing in channels respectively corresponding to the electrodes are to be the same, e.g., approximately the same.

For example, as illustrated, each of the electrodes has an impedance—for example—A1 has 30 kΩ, A2 has 30 kΩ, D1 has 40 kΩ, D2 has 20 kΩ, C1 has 30 kΩ, C2 has 30 kΩ, B1 has 40 kΩ, and B2 has 20 kΩ.

In this example, the implant system may set respective resistance values of variable resistors respectively connected to the (sub)-electrodes A1, A2, D1, D2, C1, C2, B1, and B2 to be 10 kΩ, 10 kΩ, 0 kΩ, 20 kΩ, 10 kΩ, 10 kΩ, 0 kΩ, and 20 kΩ, respectively. In such an example, a total impedance of each of the (sub)-electrodes A1, A2, D1, D2, C1, C2, B1, and B2 may be 40 kΩ, which may be the same for the electrodes, by the variable resistors. Thus, the current values flowing in the channels respectively corresponding to the electrodes may also become the same, e.g., substantially the same, and thus an impedance mismatch may not occur.

Figure 9:
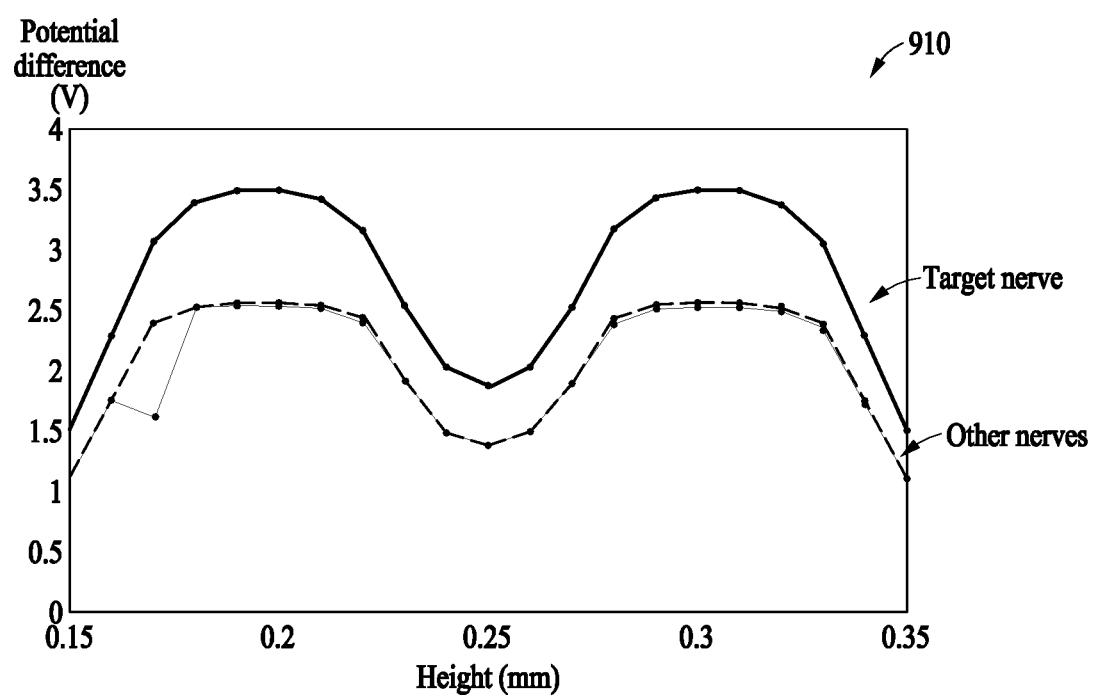
FIG. 9 illustrates an example graph of a potential difference between a target nerve and other nerves by the resistance value set according to what is described with reference to FIG. 8.

FIG. 9 illustrates an example graph of a potential difference between a target nerve and other nerves by a resistance value of a variable resistor set according to what is described with reference to FIG. 8. Referring to FIG. 9, a graph 910 indicates a result obtained by controlling eight electrodes A1, A2, B1, B2, C1, C2, D1, and D2 illustrated in FIG. 8 to have the same impedance, distributing the same voltage of 6V between four working electrodes A1, A2, D1, and D2 and four counter electrodes B1, B2, C1, and C2, and comparing an end-to-end potential difference between a target nerve and other nerves. Referring to the result, an N2 target electrode value may be reduced by 33% and the performance may be reduced by 50% at a height of 0.3 mm, compared to the result illustrated in the graph 730 of FIG. 7B.

Referring to the graph 910, other remaining nerves at a height of 0.2 mm in addition to the target nerve at the height of 0.3 mm may also have the same potential difference as the target nerve. Thus, current values flowing in the remaining nerves at the height of 0.2 mm, in addition to the target nerve at the height of 0.3 mm, may also be the same, and thus an impedance mismatch may not occur.

FIG. 10 illustrates an example of a configuration of an implant system. Referring to FIG. 10, an implant system 1000 may include an electrode array 1005, a stimulation controller 1010, a bio-interface 1020, a processor 1030, a timer 1040, a memory 1050, a power source 1060, and a connectivity 1070.

The electrode array 1005 may include electrodes to perform nerve stimulation and nerve sensing. The electrode array 1005 may be connected to the bio-interface 1020 through switches 1015 included in the stimulation controller 1010.

The stimulation controller 1010 may include variable resistors 1011, a sensor 1013, and the switches 1015. The sensor 1013 may sense an impedance of each of the electrodes included in the electrode array 1005.

The stimulation controller 1010 may address an impedance mismatch that may occur when grouping electrodes to perform sensing and using the grouped electrodes to perform stimulation, through the variable resistors 1011. The stimulation controller 1010 may also be referred to herein as an impedance controller in that it controls an impedance to perform stimulation. The stimulation controller 1010 may operate the same as the impedance controller 110 described above with reference to FIG. 1, and thus reference may be made to what is described above about the operations of the variable resistors 113 and the switches 115 of the impedance controller 110. As described above, the term "stimulation controller" and the term "impedance controller" may be used interchangeably.

The bio-interface 1020 may include a sensor 1021 and a stimulator 1023. The connection to the sensor 1021 and/or the stimulator 1023 may be controlled by the processor 1030 through the switches 1015. The sensor 1021 may measure a voltage level through the electrodes included in the electrode array 1005 and the switches 1015 included in the stimulation controller 1010. The stimulator 1023 may transmit an electrical signal to electrodes through connected switches.

In addition, the bio-interface 1020 may sense or detect various sets of bioinformation from a body of a user. The bioinformation may include, as non-limiting examples, heart rate, body temperature, blood glucose level, blood pressure, and the like, but examples are not limited thereto. The bioinformation may change in various ways depending on each applied field of an implant system.

The implant system 1000 may generate a stimulation signal or a stimulation pulse for a user based on bioinformation sensed from the body of the user. The implant system 1000 may generate a stimulation signal for the user by providing power to the bio-interface 1020.

The processor 1030 may control the switches 1015 based on a preset time using the timer 1040. For example, in a case of providing nerve stimulation, the stimulation controller 1010 may verify an impedance of each electrode, and set variable resistance values based on a stimulation pattern or algorithm predefined according to the set purpose of use of the electrodes.

The memory 1050 may store the predefined stimulation pattern or algorithm. The memory 1050 may also store various sets of data generated in the processor 1030.

The processor 1030 may receive electric power through the power source 1060.

The power source 1060 may be, for example, a battery or a wireless power receiver that is wirelessly charged, but is not limited thereto. The processor 1030 may externally transmit data, or receive a new stimulation pattern or an updated algorithm, through the connectivity 1070.

The connectivity 1070 may include both wireless and wired communication.

The implant system 1000 may be, for example, a pacemaker artificially providing a stimulation pulse when a heart function fails or temporarily stops.

FIG. 11 illustrates an example of a detailed configuration of the implant system of FIG. 10. In the example of FIG. 11, illustrated is a detailed connection among electrodes 1105, a stimulation controller 1110, and a bio-interface 1120 of an implant system 1100.

Each of the electrodes 1105, for example, Electrode #1, #2, ..., #N, may be connected to variable resistors 1111 of the stimulation controller 1110. A reference value of the variable resistors 1111 may be 0, for example. The variable resistors 1111 may respectively correspond to the electrodes 1105. To the variable resistors 1111, respective multiplexers (MUX) 1113 may be connected, corresponding to the electrodes Electrode #1, #2, ..., #N.

The electrodes 1105 may include a reference electrode (e.g., Electrode Ref.). The reference electrode may be used to provide a reference voltage.

Based on the set purpose of use of each electrode, the multiplexers 1113 may be connected to one of a recorder 1121 of the bio-interface 1120, a stimulator 1123 of the bio-interface 1120, and an impedance sensor 1117, or be set in an open state without being connected.

Based on the set purpose of use of each electrode, each of the multiplexers 1113 may be connected to Sensing #N of the recorder 1121 or Reference. Alternatively, each of the multiplexers 1113 may be connected to a cathode electrode or an anode electrode of the stimulator 1123.

For example, the recorder 1121 that performs nerve sensing may have a high impedance condition, and thus the electrodes 1105 may be used individually. In this example, the electrodes 1105 may be individually connected to the recorder 1121.

In contrast, the stimulator 1123 that performs nerve stimulation may have a low impedance condition, and thus the electrodes 1105 may be grouped or connected in parallel to be used to reduce an impedance. The impedance of the electrodes 1105 may be inversely proportional to the size of an area. Thus, by grouping or connecting electrodes in parallel, it is possible to reduce a total impedance of the electrodes and meet an impedance suitable to perform stimulation. Such parallel-connected electrodes may be grouped together with a common cathode electrode and anode electrode connected to the stimulator 1123, and thus used to perform stimulation.

The implant system 1100 may verify an impedance of each of the electrodes 1105 through the impedance sensor 1117 connected to the multiplexers 1113.

Figure 12:
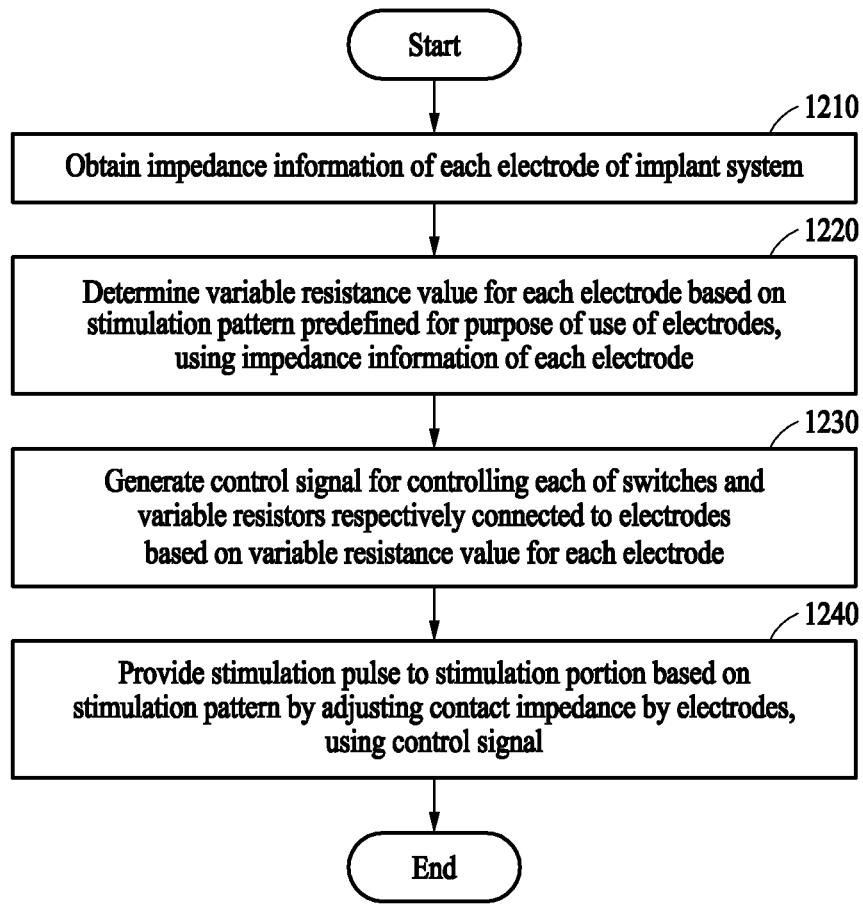
FIGS. 12 and 13 illustrate an example of an operating method of an implant system.

FIG. 12 illustrates an example of an operating method of an implant system. In an example, an implant system may provide a stimulation pulse to a stimulation portion (or a portion to be stimulated) through operations 1210 through 1240 to be described hereinafter with reference to FIG. 12.

Referring to FIG. 12, in operation 1210, the implant system obtains impedance information of each electrode of the implant system.

In operation 1220, the implant system determines a variable resistance value for each electrode based on a stimulation pattern predefined for the set purpose of use of electrodes, using the impedance information obtained in operation 1210. For example, the implant system may determine a variable resistance value for each of electrodes including target electrodes, based on the impedance information of each electrode and the target electrodes corresponding to a stimulation portion based on the stimulation pattern.

In operation 1230, the implant system generates a control signal to control each of switches and variable resistors respectively connected to the electrodes based on the variable resistance value for each electrode determined in operation 1220. For example, the implant system may generate the control signal to control each of the switches and the variable resistors respectively connected to the electrodes based on the variable resistance value for each electrode, based on at least one of the set purpose of use of the electrodes or a position of an electrode to which nerve stimulation is to be provided.

For example, in a case in which electrodes are controlled to perform nerve stimulation, the implant system may group at least a portion of the electrodes into a single channel. The implant system may reduce a contact impedance by grouping the electrodes to increase the magnitude of stimulation due to an issue of a compliance voltage, and generate a control signal to variable resistors to achieve impedance matching. Also, in a case in which electrodes perform nerve stimulation, to control a current amount of target electrodes corresponding to a certain portion among the electrodes, the implant system may generate a control signal to perform switches connected to the target electrodes and an electrode impedance for each of the target electrodes.

For another example, in a case in which electrodes are configured to perform general nerve stimulation, the implant system may generate a control signal to variable resistors respectively connected to the electrodes such that respective current values flowing in channels respectively corresponding to the electrodes become the same, e.g., substantially the same.

Depending on examples, the implant system may set a timer based on a time that is set based on a sensing period of sensing impedance information of each electrode and a stimulation period of a stimulation pulse. In such a case, the implant system may generate a control signal to control each of switches and variable resistors respectively connected to electrodes based on a time set by the timer.

In operation 1240, the implant system provides a stimulation pulse to a stimulation portion based on the stimulation pattern by controlling a contact impedance by the electrodes, using the control signal generated in operation 1230.

Figure 13:
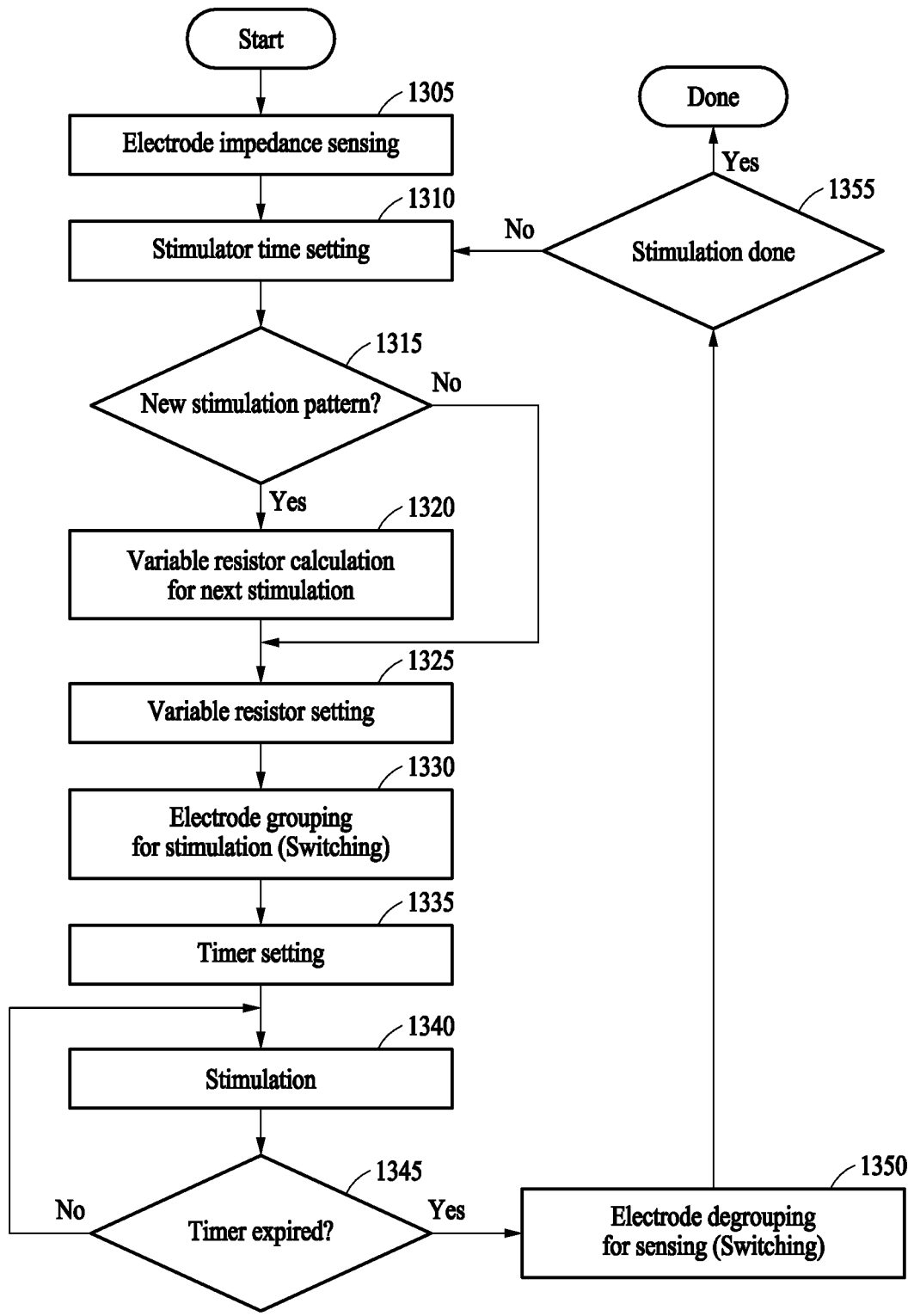

FIG. 13 illustrates another example of an operating method of an implant system. In an example, an implant system may perform a switching operation to optimize electrodes in each application through operations 1305 through 1355 to be described hereinafter with reference to FIG. 13.

Referring to FIG. 13, in operation 1305, a processor of the implant system senses an impedance of each electrode of the implant system.

In operation 1310, the implant system sets a time of a timer for a stimulator or a sensor by verifying a stimulation and sensing period.

In operation 1315, the implant system verifies whether there is a new stimulation pattern before applying a stimulation pulse. In operation 1325, when it is verified in operation 1315 that there is no new stimulation pattern, the implant system sets a variable resistance value of variable resistors based on a stimulation portion that is based on a preset stimulation pattern, and on impedance information of each electrode that is sensed in operation 1305.

In operation 1320, when it is verified in operation 1315 that there is a new stimulation pattern, the implant system calculates a variable resistance value for a new stimulation pulse. A stimulation portion and/or a magnitude of a stimulation waveform may vary by stimulation pattern, and thus the implant system may calculate a new variable resistance value that is suitable for the new stimulation pattern. In operation 1325, the implant system sets the variable resistance value calculated in operation 1320 for the variable resistors. The variable resistance value set in operation 1325 may correspond to a value of variable resistance for each electrode when a stimulation pulse is applied.

In operation 1330, the implant system groups electrodes to provide nerve stimulation. Here, depending on the set purpose being to perform stimulation, a position of an electrode, the number of electrodes to be used, and the set variable resistance value may vary. The set purpose of the stimulation may be for nerve stimulation and/or nerve sensing, but examples are not limited thereto. For example, in operation 1330, the implant system may turn on switches respectively connected to the electrodes for nerve stimulation to group the electrodes into one channel.

In operation 1335, the implant system sets a timer to perform stimulation or sensing based on the time set in operation 1310. In operation 1340, the implant system continuously provides a stimulation pulse while the timer is operating.

In operation 1345, the implant system determines whether the timer is expired. When it is determined in operation 1345 that the timer is not expired, the implant system continuously provides the stimulation pulse in operation 1340.

In operation 1350, when it is determined in operation 1345 that the timer is expired, the implant system degroups the electrodes, i.e., the electrodes that were grouped to perform stimulation, in operation 1330 in order to perform nerve sensing. For example, in operation 1350, the implant system may set resistance values of variable resistors respectively connected to the electrodes to be equal (e.g., substantially equal) such that current values flowing in channels corresponding to the electrodes are to be equal. In operation 1350, the implant system may turn on one of the switches respectively connected to the electrodes to perform nerve sensing.

In operation 1355, the implant system determines whether the provision of stimulation is completed. When it is determined in operation 1355 that the provision of stimulation is completed, the implant system terminates the operations.

However, when it is determined in operation 1355 that the provision of stimulation is not yet completed, for example, when another stimulation by the new stimulation pattern is scheduled subsequently, the implant system sets a time of a timer for the next stimulation in operation 1310. Subsequently, the implant system newly sets a variable resistance value of variable resistors, based on a stimulation portion that is based on the new stimulation pattern and on impedance information of each electrode sensed in operation 1305, and repeatedly performs the operations described in the foregoing to provide stimulation based on the new stimulation pattern.

The implant system, and other apparatuses, devices, units, modules, and components described herein with respect to FIGS. 1-13 are implemented by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-13 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, as well as one or more systolic arrays in combination therewith as a non-limiting example, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above.

In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions used herein, which disclose algorithms for performing the operations that are performed by the hardware components and the methods as described above.

The instructions or software to control computing hardware, for example, one or more processors or computers, as well as one or more systolic arrays in combination therewith, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD–Rs, CD+Rs, CD–RWs, CD+RWs, DVD-ROMs, DVD–Rs, DVD+Rs, DVD–RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents.

What is claimed is:
1. An implant system comprising:
plural electrodes;
an impedance controller configured to selectively connect at least a portion of the plural electrodes between a stimulator to perform nerve stimulation and a sensor to perform nerve sensing based on a control signal, and set an impedance of each of the plural electrodes; and a processor configured to determine a variable resistance value for each of the plural electrodes based on a stimulation pattern predefined according to a selectively set purpose of use of the plural electrodes, and generate the control signal to control a corresponding contact impedance by the plural electrodes, wherein at least a portion of the plural electrodes are used for both nerve sensing and nerve stimulation.

2. The system of claim 1, wherein the processor generates the control signal to control at least one of plural switches connected respectively to the plural electrodes, or variable resistors connected respectively to the plural electrodes, based on the selectively set purpose of the plural electrodes or based on the selectively set purpose of the plural electrodes and a position of an electrode to which nerve stimulation is to be provided.

3. The system of claim 2, wherein the processor is configured to:
determine whether to group the plural electrodes based on the set purpose of use of the plural electrodes; and
generate the control signal to selectively control the switches to connect the plural electrodes between the sensor and the stimulator based on the set purpose, including the processor being configured to generate the control signal to control the switches to connect the plural electrodes to the sensor when the set purpose of use of the plural electrodes is to perform sensing, and configured to alternately generate the control signal to control the switches to connect the plural electrodes to the stimulator when the set purpose of use of the plural electrodes is to perform stimulation.

4. The system of claim 2, wherein the processor is configured to:
determine whether to group the plural electrodes, or to group a portion of the plural electrodes, based on at least one of the set purpose of use of the plural electrodes, a position to which nerve stimulation is to be provided based on the set purpose, or a direction in which nerve stimulation is to be provided.

5. The system of claim 2, wherein, for when the set purpose of use of the plural electrodes is to perform nerve stimulation, the processor is configured to:
group at least a portion of the plural electrodes into one channel; and
generate the control signal for the variable resistors respectively connected to the plural electrodes such that a contact impedance by the grouped electrodes stimulates a target stimulation portion.

6. The system of claim 2, wherein, for when the set purpose of use of the electrodes is to perform nerve stimulation, the processor is configured to:
generate the control signal to control an electrode impedance of each of plural target electrodes corresponding to a portion of a nerve among the plural electrodes to control a current amount of the plural target electrodes.

7. The system of claim 2, wherein, for when the set purpose of use of the plural electrodes is to perform nerve sensing, the processor is configured to:
generate the control signal for the variable resistors respectively connected to the plural electrodes to allow current values flowing in channels respectively corresponding to the plural electrodes to be equal.

8. The system of claim 2, wherein the processor is configured to:
provide nerve stimulation by obtaining an impedance of each of the plural electrodes through the sensor and controlling a variable resistor for each of the plural electrodes based on the impedance of each of the plural electrodes.

9. The system of claim 2, wherein the processor is configured to:
control at least one of the switches or the variable resistors by generating the control signal based on a time set by a timer.

10. The system of claim 2, wherein the impedance controller comprises:
a plurality of sensors each configured to sense an electrode impedance of each of the plural electrodes;
the variable resistors each configured to control the electrode impedance of each of the plural electrodes; and
the switches each configured to selectively connect each of the plural electrodes between the stimulator and the sensor.

11. The system of claim 2, wherein the sensor is configured to:
perform nerve sensing by measuring a voltage level through the plural electrodes and the switches.

12. The system of claim 1,
wherein the impedance controller comprises switches, and
wherein the stimulator is configured to: perform nerve stimulation by providing an electrical signal to an electrode among the plural electrodes through the switches.

13. An implant method, the method comprising:
obtaining impedance information of each of plural electrodes of the implant system;
determining a variable resistance value for each of the plural electrodes based on a stimulation pattern predefined according to a selectively set purpose of use of the plural electrodes, using the impedance information of each of the plural electrodes;
generating a control signal for controlling each of switches and variable resistors respectively connected to the plural electrodes based on the variable resistance value for each of the plural electrodes; and
providing a stimulation pulse to a stimulation portion based on the stimulation pattern by controlling a contact impedance by the plural electrodes, based on the control signal,
wherein at least a portion of the plural electrodes are used for both nerve sensing and nerve stimulation.

14. The method of claim 13, wherein the determining of the variable resistance value for each of the plural electrodes comprises:
determining a variable resistance value for each of the plural electrodes including target electrodes corresponding to the stimulation portion based on the stimulation pattern, based on the impedance information of each of the plural electrodes and the target electrodes.

15. The method of claim 13, wherein the generating of the control signal comprises:
generating the control signal to control each of the switches and the variable resistors respectively connected to the plural electrodes based on the variable resistance value for each of the plural electrodes, using at least one of the set purpose of use of the plural electrodes or a position of an electrode to which nerve stimulation is to be provided.

16. The method of claim 15,
wherein the set purpose of use of the electrodes is to perform nerve stimulation, and
wherein the generating of the control signal comprises:
grouping at least a portion of the plural electrodes into one channel; and
generating the control signal for the variable resistors respectively connected to the plural electrodes such that a contact impedance by the grouped electrodes stimulates a target stimulation portion.

17. The system of claim 1, wherein some of the plural electrodes used for nerve sensing are grouped and the grouped electrodes are used for nerve stimulation.

18. The system of claim 17, wherein the grouped electrodes are connected in parallel.

19. The system of claim 17, wherein a current amount of each of the grouped electrodes are controlled to provide intended stimulation.

20. The system of claim 2, wherein the processor is configured to:
generate the control signal to control a position of a target electrode to which nerve stimulation is to be provided based on the set purpose of use of the plural electrodes, the number of target electrodes, and a setting value of a variable resistor connected to the target electrode, based on the set purpose of use of the plural electrodes.

* * * * *